United States Patent

Stone et al.

[11] Patent Number: 6,139,565
[45] Date of Patent: *Oct. 31, 2000

[54] SUTURE ANCHOR ASSEMBLY

[75] Inventors: Kevin R. Stone, 1 Throckmorton La., Mill Valley, Calif. 94941; Allen H. DeSatnick, Marblehead, Mass.

[73] Assignee: Kevin R. Stone, Mill Valley, Calif.

[*] Notice: This patent is subject to a terminal disclaimer.

[21] Appl. No.: 09/174,829

[22] Filed: Oct. 19, 1998

Related U.S. Application Data

[63] Continuation of application No. 08/665,528, Jun. 18, 1996, Pat. No. 5,824,011, which is a continuation of application No. 08/388,951, Feb. 15, 1995, abandoned, which is a continuation-in-part of application No. 08/349,677, Dec. 5, 1994, Pat. No. 5,443,482, which is a continuation of application No. 08/081,516, Jun. 23, 1993, Pat. No. 5,370,662.

[51] Int. Cl.[7] ................................................ A61B 17/04
[52] U.S. Cl. ........................................ 606/232; 606/73
[58] Field of Search .................... 606/72–75, 60, 606/61, 104, 219, 220, 232

[56] References Cited

U.S. PATENT DOCUMENTS

| | | | |
|---|---|---|---|
| 4,968,315 | 11/1990 | Gatturna et al. | 606/232 |
| 5,102,421 | 4/1992 | Anspach, Jr. | 606/232 |
| 5,207,679 | 5/1993 | Li | 606/232 |

*Primary Examiner*—Gary Jackson
*Attorney, Agent, or Firm*—McDermott, Will & Emery

[57] ABSTRACT

Suture anchor assembly for attaching soft tissue to bone. The assembly (10) includes an elongated member (12) having a continuous self-tapping threaded anchor portion (14) having a self-drilling contour at its proximal end, and an integral eyelet (18) for receiving a suture (30) at its distal end. The distal end further includes a receiver for a rotating driver device (20), such as a cannulated drill. The assembly (10) is designed for endoscopic insertion of the anchor (14), with the suture (30) extending along the central axis ($X_1$) of the driver (20).

13 Claims, 10 Drawing Sheets

SUTURE ANCHOR ASSEMBLY

REFERENCE TO RELATED APPLICATION

This application is a continuation of application Ser. No. 08/665,528, filed Jun. 18, 1996, now U.S. Pat. No. 5,824,011, which is a continuation of application U.S. Ser. No. 08/388,951, filed Feb. 15, 1995, now abandoned, which is a continuation-in-part of application Ser. No. 08/349,677, filed Dec. 5, 1994, now U.S. Pat. No. 5,443,482, which is a continuation of U.S. application Ser. No. 08/081,516, filed Jun. 23, 1993, now U.S. Pat. No. 5,370,662.

BACKGROUND OF THE INVENTION

The present invention generally relates to suture anchors. Specifically, the invention relates to suture anchors used in securing soft tissue to bone.

Soft tissues, such as tendons and ligaments generally insert into bone through small collagenous fibers called sharpey's fibers. These connections are strong and permit the muscle which pull on the tendons to effect force on the bones, or the ligaments which stabilize the body's joints, the resist force. When a tissue is torn away from the bone and requires repair, the surgeon is often required to fashion tunnels into the bone through which to pass sutures, which are then threaded through the soft tissues. The bone tunnels are often difficult to make, and generally require large open incisions. Recently, through the advent of endoscopic surgery, where the surgeon looks into a joint cavity with a telescope, there has been a desire to repair soft tissues back to bone without performing a large open incision. The device described herein facilitates that procedure.

A variety of devices are available for attaching objects to bone, such as screws, staples, cement, and sutures alone. These devices have been used to attach soft tissue, such as ligaments, tendons, muscles, as well as objects such as prostheses, to bone. Screws tend to loosen with time, usually requires a second operation to remove the loosened screw. In addition, conventional screws tend to be time-consuming and difficult to install, especially in a tight space such as that encountered during endoscopic surgery.

Installation of presently available bone screws involves several steps. First, a pilot hole must normally be drilled into the bone. Then, depending on the bone structure, the bone may also have to be tapped to accept to the screw. The screw is next positioned and turned to fasten. Finally, if the suture is not preattached, the suture is threaded into an eyelet contained in the screw. This multi-step process, necessitated by the structure of available bone screw devices, is difficult for the surgeon, especially in confined surgical areas. Often, such accessibility considerations limit the ability of the surgeon to secure sutures at optimal locations, forcing the surgeon to select a less-than-desirable location. Furthermore, the final position of the screw is determined once the hole has been drilled, making it difficult to relocate or position the screw in a different position.

U.S. Pat. No. 4,632,100 discloses a cylindrical suture anchor which includes a drill at a first end (for boring a hole in a bone) and a flight of threads on the other end, and distal from the drill, for securing the anchor in a hole established by the drill. Sutures are held in the interior of the anchor by means of an annular disc that is press fit into the interior of the anchor. This two piece assembly is difficult to assemble and, due to the suture-holding disc, is substantially limited in the number of sutures that can be held. Moreover, the discrete drill and thread flights are inefficient in their operation.

Staples are disadvantageous for some of the same reasons as standard screws, plus there are additional set-backs for using staples for attachment. Staples have been known to crack the bone during deployment, or to accidentally transect the object being attached to the bone.

Other devices that currently exist for attaching soft tissue to bone include metal screws with sutures attached, shaped metal anchors through which sutures can be threaded, and plastic tacks with sutures attached. Each of these devices includes a single suture affixed to the device prior to implantation. These devices are difficult to deploy endoscopically and are limited to single sutures even though multiple sutures are often required for soft tissue repair.

Accordingly, it is an object of the invention to provide a device that is designed for endoscopic use and that accommodates multiple suture fixation.

SUMMARY OF THE INVENTION

The present invention generally relates to suture anchor assemblies of the type used for securing soft tissue to bone. The inventive assembly includes an elongated, generally cylindrical member having an anchor portion at a first end and a suture/drive portion at a second end. An eyelet is positioned at the second end for receiving and securing a suture. The second end also includes a coupler for coupling a cannulated driver to the anchor to enable insertion of the anchor into bone.

The cylindrical member of the anchor assembly generally extends along a central axis X, and has a maximum outer diameter D. The anchor portion includes a self-drilling contour near the first end. Both the anchor portion and the suture/drive portion have a continuous self-tapping thread pattern on their outer surfaces.

The eyelet is positioned near the second end such that a suture path is defined from the region adjacent to the second end, through the eyelet and back to the region adjacent to the second end. The endpoints of the suture path are less than $D'/2$ from the central axis. In a preferred form of the invention, $D'$ is less than the maximum outer diameter of the cylindrical member D.

The coupler that forms part of the suture/driver end of the cylindrical member is adapted to mechanically couple a distal tip of a cannulated driver. The driver may have an inner diameter greater than or equal to the diameter $D_1$ of the suture/driver end and an outer diameter less than or equal to diameter D. The driver is rotatable about a drive axis and thus rotates the cylindrical member about that drive axis when the distal tip of the driver is mechanically coupled with the coupler.

In another embodiment, the coupler includes at least first and second planar flanges located at opposite sides of the central axis, and extending radially outward from the central axis in opposite directions. The coupler may further include third and fourth planar flanges, also on opposite sides of and extending radially outward from the central axis. The flanges function as stop-points, or form a shoulder, to prevent the cylindrical member from being inserted beyond a predetermined point into the bone.

The coupler may also include one or more pairs of grooves in the side of the cylindrical member and extending from the second end to the first end. The grooves extend along groove axes essentially parallel to the central axis. Each groove of each pair of grooves is located on opposite sides of the cylindrical member, and the respective opposing groove axes are essentially coplanar with the central axis.

In another embodiment the suture anchor assembly of the present invention further includes a cannulated driver with a distal tip having an inner diameter $D_2$ which is greater than or equal to D'. The cannulated driver can include an annular tapered leading edge.

In another embodiment, the anchor portion includes a self-drilling contour at least at points near the first end.

In yet another embodiment, the anchor portion and the suture/drive portion have a continuous self-tapping thread pattern on their outer surfaces. The thread pattern extends at least from points near the first end to points near the second end.

The anchor portion can include drilling means at its distal tip for establishing a hole in bone. The suture/drive portion includes an eyelet which is bounded by a pair of channels extending axially therein from the second end of the cylindrical member. The channels are on opposite sides of the suture/drive portion and are linked by a central aperture. The channels can be either external or internal.

BRIEF DESCRIPTION OF THE FIGURES

The invention is further described by the following description, and Figures in which.

Like elements in the respective FIGURES have similar reference numbers.

DESCRIPTION OF THE PREFERRED EMBODIMENT

The suture anchor assembly of the present invention primarily is for use during endoscopic surgery. The anchors are intended for permanent implantation into a patient, however it is possible to remove the anchors if necessary. The use of suture anchors that fix soft tissue to bone is frequent in orthopedic surgery, though such anchors may be used in other fields as appropriate.

Figure 1:
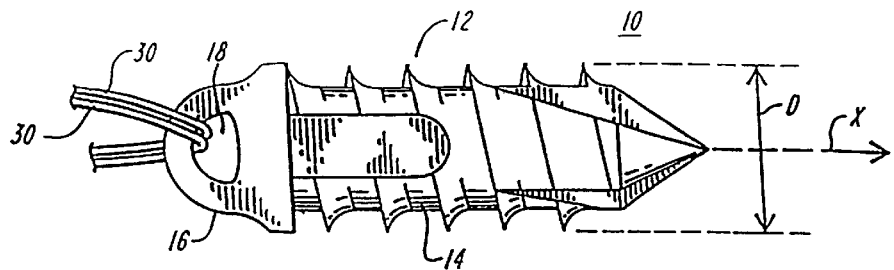
FIG. 1 shows a side plan view of one embodiment of the suture anchor assembly of the present invention.
Figure 2:
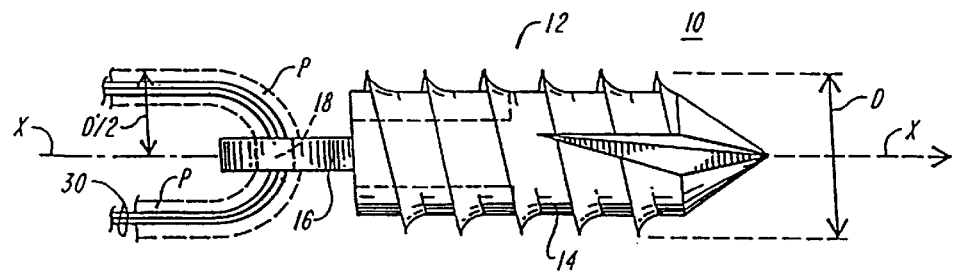
FIG. 2 shows an alternate side plan view of the embodiment of FIG. 1 rotated 90° from FIG. 1.

Generally, and as illustrated in FIGS. 1 and 2, the inventive suture anchor assembly 10 includes an elongated cylindrical member 12. The cylindrical member 12 includes a threaded anchor portion 14 at one end and a suture/drive portion 16 at the opposite end. The suture/drive portion 16 is adapted for insertion into the distal end of a driver 20, such as a standard operating room cannulated drill. The inventive assembly 10 is thus adapted for installation into a patient by endoscopic means, or any other appropriate surgical procedure. The inventive assembly 10 may include several different embodiments illustrated and described herein.

Preferably, the cylindrical member 12 is manufactured from stainless steel, titanium, or some other durable, non-degradable, biocompatible material. Alternatively, the cylindrical member 12 may be manufactured from a non-biocompatible material, but coated with a biocompatible substance prior to insertion in the patient. The assembly 10 may be manufactured as a single piece, using standard metal-shaping techniques. Alternatively, the top portion 16 may be manufactured separately from the bottom anchor portion 14 and attached by conventional methods and materials. In such an embodiment, the two separate portions may be manufactured using the same or different materials.

In one form, the anchor portion 14 may be metal, forming a permanent element, while the suture/drive portion 16 may be made of a bioresorbable material (which will be resorbed after residing in a patient). The latter form is particularly useful where it is the eventual goal to have no protuberance beyond the bone surface.

The threaded anchor portion 14 of the cylindrical member 12 covers a portion of the surface of that member 12. The actual amount of threaded anchor portion 14 may depend upon several variables, such as the type of tissue, the type of anticipated surgical procedure in which the assembly will be used, manufacturing limitations, materials limitations, and other variables readily determinable by one skilled in the relevant art.

The top suture/driver portion 16 at the distal end of the assembly 10 is designed both to hold a suture material and to fit the head of a driver device. In the illustrated embodiment of FIG. 1, the top portion 16 includes an eyelet 18 of sufficient size to receive one or more sutures 30. Since sutures are made of different materials and, consequently, are available in a variety of different diameters, the actual size of the eyelet 18 may be of a standard size to accept any suture material or may come in a range of sizes specific to different suture types.

Figure 5:
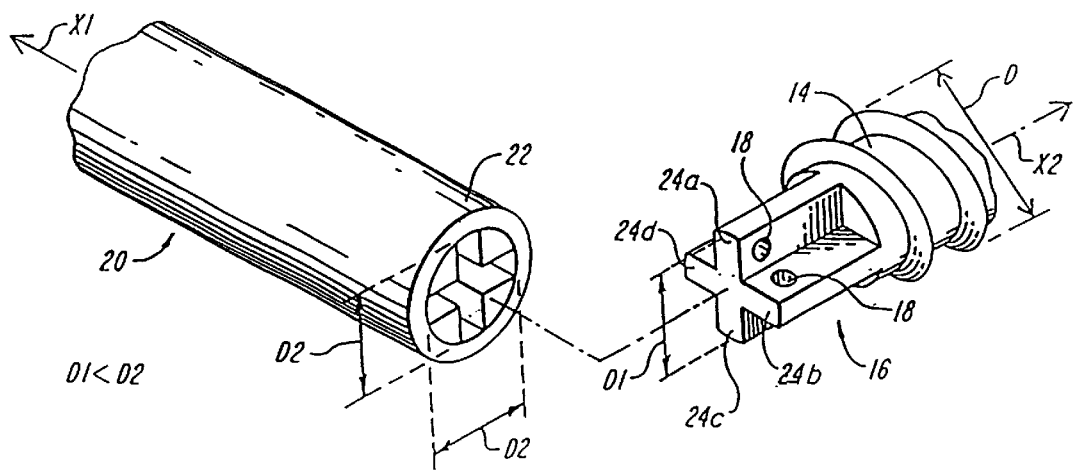
FIG. 5 shows a perspective view of another embodiment of the inventive suture anchor assembly, including the distal portion of a driver assembly.

In alternative embodiments, and as exemplified in FIG. 5, the top portion 16 may includes a plurality of aligned eyelets 18 to enable one or more sutures to pass through two or more such eyelets 18. Alternatively, multiple sutures may pass through any one of the eyelets. The suture 30 is preferably prethreaded in the suture anchor 10, but may be threaded once the anchor assembly 10 is positioned. Generally, the suture 30 passes through a suture path P through eyelet 18. The outermost boundary of suture path P is less than distance D'/2 from the central (X) axis of anchor 10, i.e. within the cylindrical regional diameter (D, where D'≦D) defined by the greatest diameter of the cylindrical member 12. This restriction on the diameter of path P is necessitated by the requirement that the top portion 16 (and suture 30) fit into a distal tip 22 of a cannulated driver assembly 20, as shown in FIG. 3.

Figure 3:
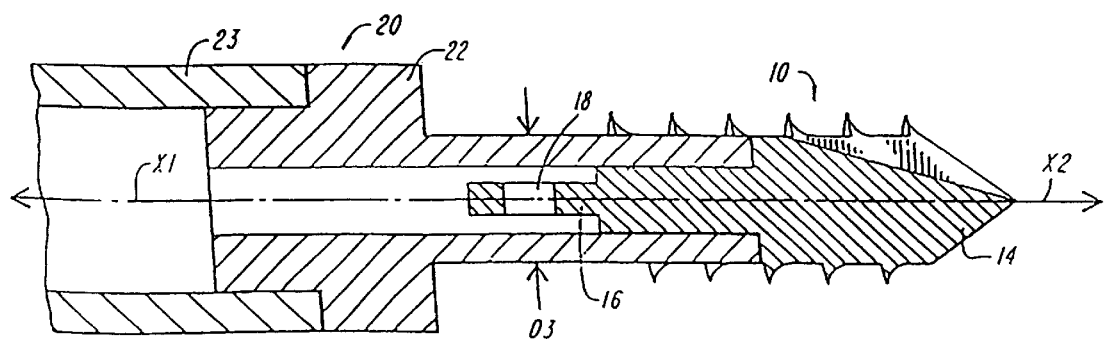
FIG. 3 shows a longitudinal cross-section view of a driver assembly engaging the suture anchor assembly of FIG. 1.

FIG. 3 illustrates the driver assembly 20 interfitted with the anchor assembly 10 of FIGS. 1 and 2. As shown, the driver assembly 20 includes a distal tip element 22 that extends from a cannulated member 23. The distal tip element 22 interfits with suture/drive portion 16. The outer diameter $D_3$ of the distal tip 22 preferably is less than or equal to outer diameter D of the cylindrical member. This reduces the amount of trauma to surrounding tissue during insertion of the assembly 10.

As shown in the Figures, the anchor portion 14 of the cylindrical member 12 is preferably self-tapping. The tip of the anchor portion 14 may taper to a point, or may be blunt-ended depending upon the specific environment in which the suture anchor assembly 10 will be used. Other tapered configurations may be used. In a preferred embodiment, and as illustrated, the tip is pointed to facilitate inserting the anchor assembly 10 at an optimal location selected by the user.

The outermost diameter D, as measured at the widest portion of the cylindrical member 12, may vary depending upon such variables as the specific environment for which the assembly 10 will be used, the materials from which the assembly 10 is manufactured, and other variables readily determined by one skilled in the relevant art. In a preferred form of the invention, the cylindrical member 12 of a typical assembly may have D approximately equal to 0.2 inches.

The top portion of the cylindrical member adjacent to the top portion may include a shoulder 17 that extends beyond the diameter D of the cylindrical member 12, as shown in FIG. 1. Thus, the shoulder 17 may consist of a set of discrete shoulder flanges, or may be a continuous portion of the top of the cylindrical member that extends beyond diameter D. The shoulder 17, whether in the form of discrete flanges or a continuous extension portion, functions to stop insertion of the anchor assembly 10 into the bone beyond the shoulder 17. Thus, the shoulder 17 prevents a user from inserting the assembly 10 so far into the bone that the suture/driver portion 16 becomes lodged in the bone.

In a preferred form of practicing the present invention, the suture/drive portion 16 is adapted to fit into the chuck of a standard operating room cannulated drill generally commercially available. In other forms of practicing the invention, a driver assembly 20 may be used having a distal tip element 22 adapted to interfit with the suture/drive portion 16 of the inventive assembly. In a preferred form of the invention, and as best shown below in conjunction with FIG. 4, the inner diameter $D_2$ of the driver tip 22 is greater than or equal to the diameter $D_1$ of suture/drive portion 16.

The distal tip 22 is cannulated to allow the suture/drive portion 16, with sutures in place in the suture path, to extend into the distal tip element 22. In one embodiment, the drive assembly 20 is cannulated, however it may only be necessary for the tip 22 to be cannulated an amount sufficient to receive the suture/drive portion 16, with sutures.

In a preferred form of practicing the present invention, the driver assembly 20 is rotatable about an axis $X_1$, which axis $X_1$ is coaxial with a central axis $X_2$ along which the cylindrical member 12 extends. Thus, when the anchor assembly 10 is engaged with the drive assembly 20, the drive assembly 20 rotates the anchor assembly 10 in such a manner as to screw the anchor 10 into the target bone.

Figure 4:
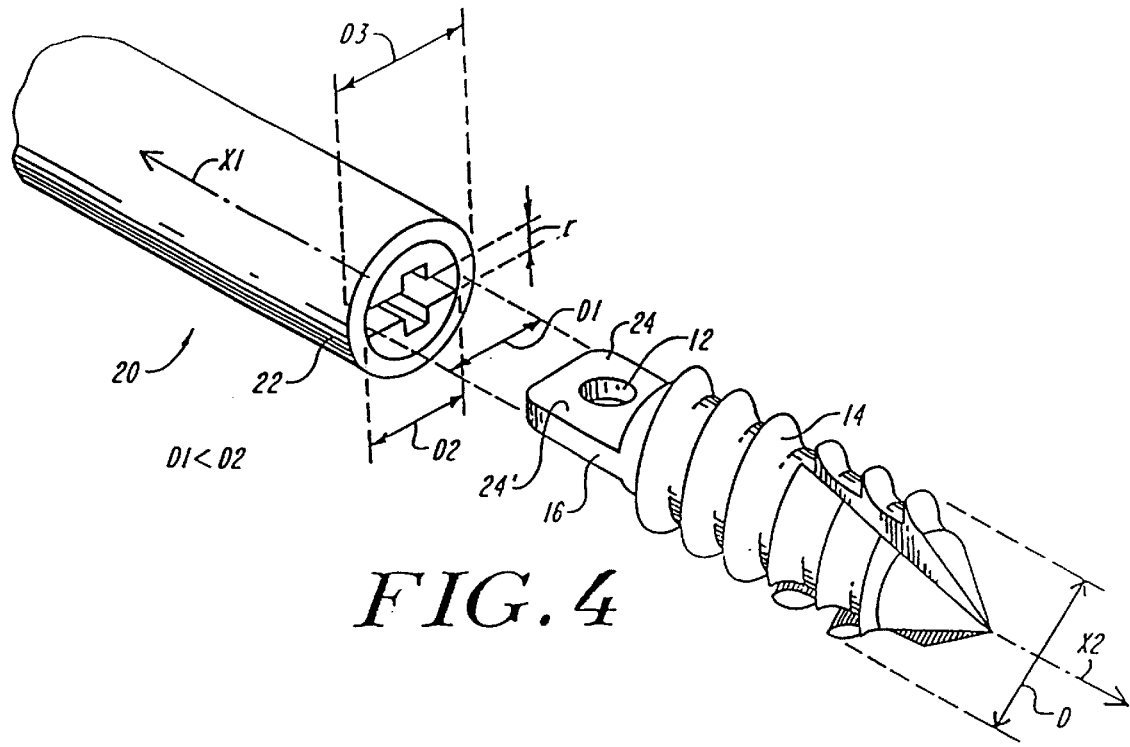
FIG. 4 shows a perspective view of another embodiment of the inventive suture anchor assembly, including the distal portion of a driver assembly.

In the illustrated embodiment of FIG. 4, the suture/drive portion 16 consists of a pair of planar flanges 24, 24' extending radially outward from and on either side of the central axis $X_2$. A suture eyelet 18 extends through the flanges 24, 24'. The distal tip element 22 of driver 20 has an inner geometry that is complementary to the outer geometry of flanges 24, 24', so that the distal tip element can engage the flanges for rotational driving.

In an alternative embodiment shown in FIG. 5, the suture/drive portion 16 includes four planar flanges, 24a, 24b, 24c, and 24d, each flange positioned about 90° from the other about the central axis. The generally "+"-shaped cross-section formed by the planar flanges then inserts into a complementary pattern in the driver distal tip element 22.

Figure 6:
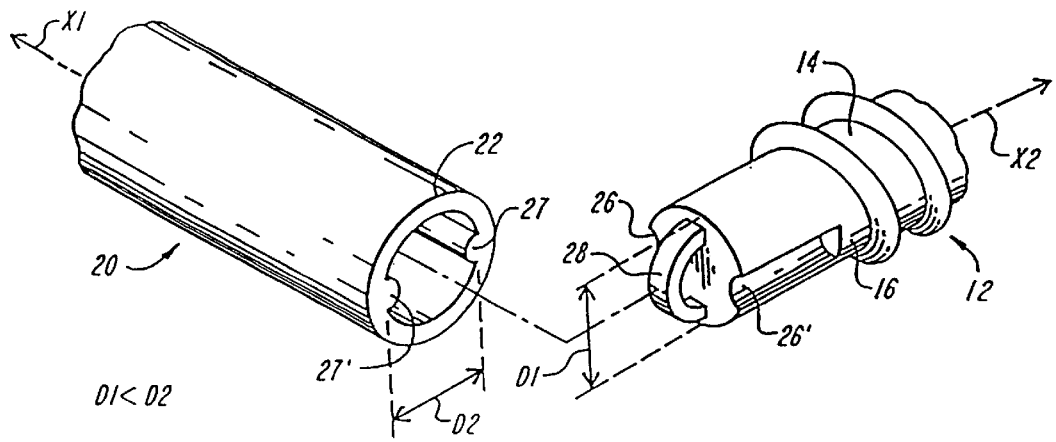
FIG. 6 shows a perspective view of another embodiment of the inventive suture anchor assembly, including the distal portion of a driver assembly.

In yet another embodiment, shown at FIG. 6, the cylindrical member 12 includes a pair of grooves 26, 26' extending from the suture/drive portion end of the member 12. The grooves 26 may extend either the entire length of the cylindrical member 12, or, as shown in FIG. 6, may extend only a portion of the way down the member 12. The exact length and depth of each groove depends on such variables and considerations as manufacturing constraints, the type of driver used, and other variables readily discernible by one skilled in the relevant art. For this form of the invention, the distal tip element 22 of driver 20 includes a pair of ridges 27, 27' that are complementary to grooves 26, 26', so that the driver 20 can engage the end of member 12.

Figure 6A:
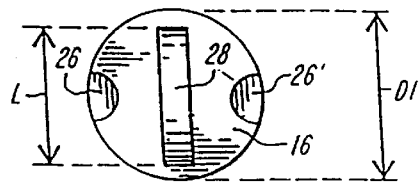
FIG. 6A shows an end view of the suture anchor assembly of FIG. 6.

As shown in the top plan view of this embodiment of the assembly 10 in FIG. 6A, a structure 28 may be provided solely for the suture eyelet 18. As illustrated, the eyelet structure 28 has a length L less than or equal to the diameter D of the cylindrical member. The structure 28 is positioned at the end of the cylindrical member 12 opposite the anchor portion 14. The structure may be integral to the cylindrical member 12 or may be mechanically or otherwise attached to the cylindrical member 12.

Figure 7:
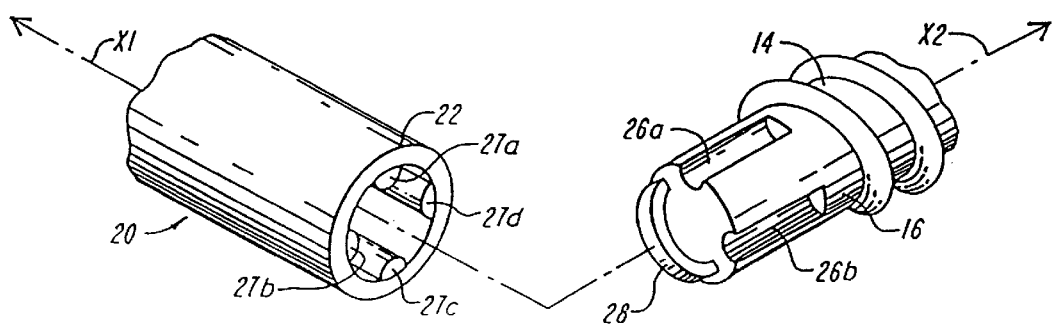
FIG. 7 shows a perspective view of another embodiment of the suture anchor assembly of the present invention, including the distal portion of a driver assembly.
Figure 7A:
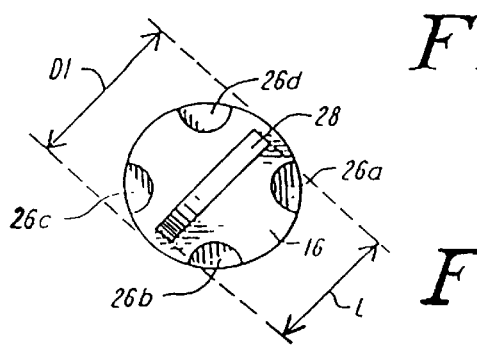
FIG. 7A shows an end view of the suture anchor assembly of FIG. 7.

In another alternative embodiment, and as illustrated in FIG. 7, the inventive assembly 10 may include a plurality of grooves 26a, 26b, 26c, and 26d positioned in predetermined locations about the surface of the cylindrical member 12. These grooves 26a, 26b, 26c, and 26d, are structurally similar to the grooves 26 and 26' described in relation to FIG. 6. As further illustrated in FIG. 7A, this illustrated embodiment includes a suture structure 28 having characteristics to the similar structure 28 described above in conjunction with FIGS. 6 and 6A. The distal tip element 22 of driver 20 for the anchor of FIGS. 7 and 7A includes four internal ridges 27a, 27b, 27c, and 27d.

Yet another embodiment of the anchor 10 is shown in FIGS. 8A, 8B, 8C and 8D. That anchor is generally similar to that of FIG. 5, except that the member 12 includes a square cross-section central bore 40 extending along its central axis $X_2$, having dimensions $d/\sqrt{2} \times d/\sqrt{2}$. In this element, a flanges 50, 52, 54 and 56 each include a respective one of suture eyelets 50a, 52a, 54a and 56a, and determine suture paths positioned such that all points are separated from the central axis $X_2$ by a distance greater than d/2.

Figure 8A:
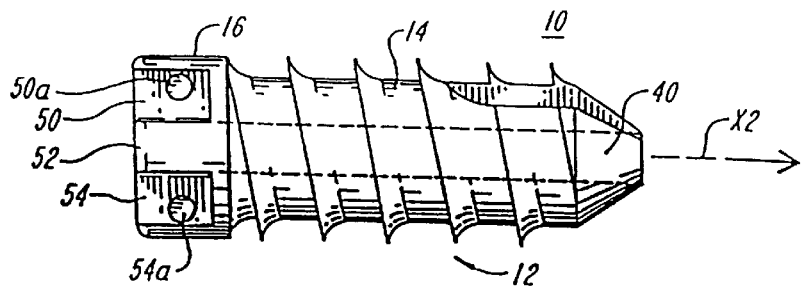
FIG. 8A shows a side plan view of another embodiment of the inventive suture anchor assembly.
Figure 8B:
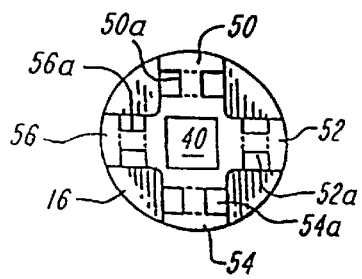
FIG. 8B shows an end view of the suture anchor assembly of FIG. 8A from the drive end.
Figure 8D:
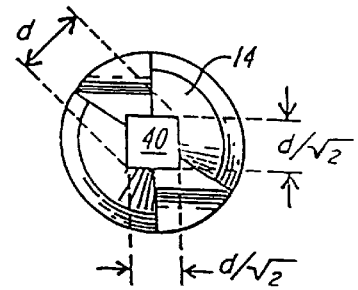
FIG. 8D shows an end view of the suture anchor assembly of FIG. 8A from the anchor end.
Figure 8C:
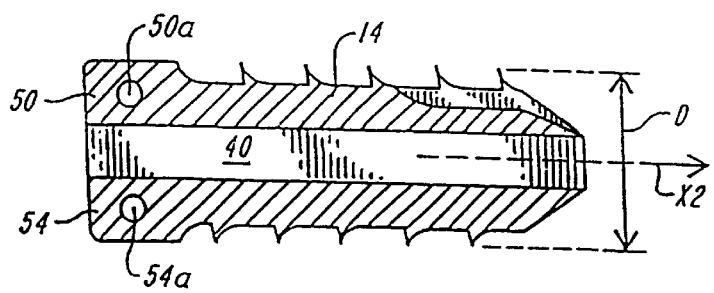
FIG. 8C shows a longitudinal cross-section of the suture anchor assembly of FIG. 8A.
Figure 8E:
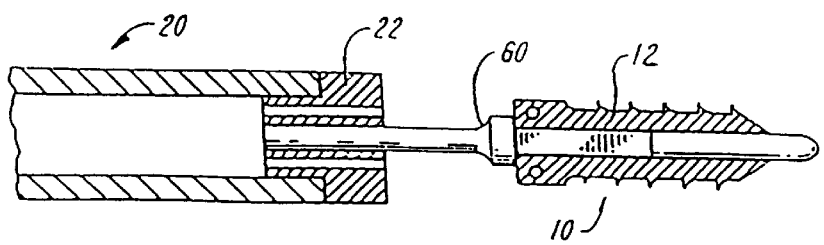
FIG. 8E shows a cross-section of the anchor of FIG. 8A together with a drive assembly.
Figure 8F:
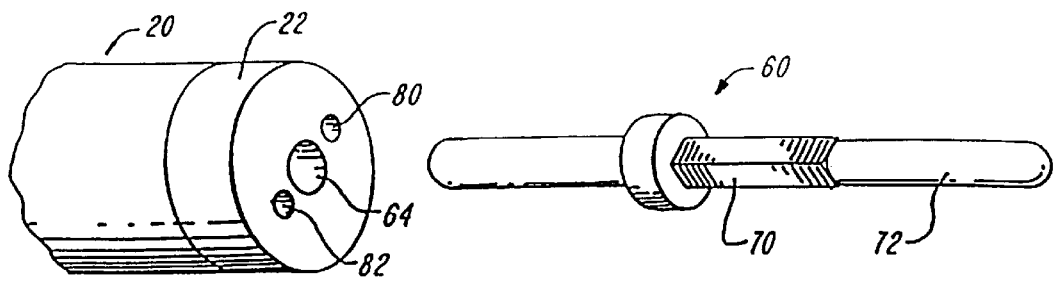
FIG. 8F shows an exploded perspective view of the driver of FIG. 8E.

The anchors of FIGS. 8A–8D are particularly adapted for driving with a square cross-section driver positioned in the central bore 40. FIGS. 8E and 8F show a cannulated driver 20 having a tip 22 which supports a drive element 60 extending from an aperture 64 in tip 22. The drive element 60 includes a square cross-section portion 70 (for driving anchor 10) and a cylindrical lead portion 72 (for guiding the lead tip of anchor 10 into a pilot hole in the target bore). In this configuration, the tip 22 also includes apertures 76 and 78 to define a suture path between the eyelets of anchor 10 and the interior of cannulated driver 20.

FIGS. 9A and 9B and FIGS. 10A and 10B show additional embodiments of the invention. The anchors of these figures include shoulders 17, which serve to limit the insertion depth of the anchors. Also these embodiments include different exemplary suture eyelet configuration compared with the configurations of the other figures.

Figure 9A:
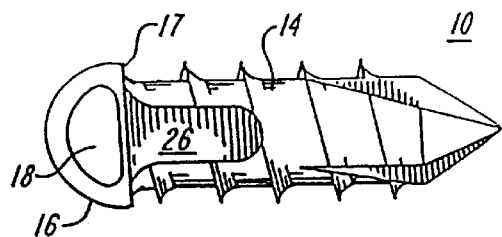
FIG. 9A shows a side plan view of another embodiment of the inventive suture anchor assembly.
Figure 9B:
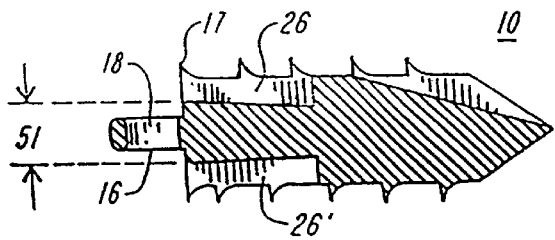
FIG. 9B shows a cross-section of the suture anchor assembly of FIG. 9A.
Figure 10A:
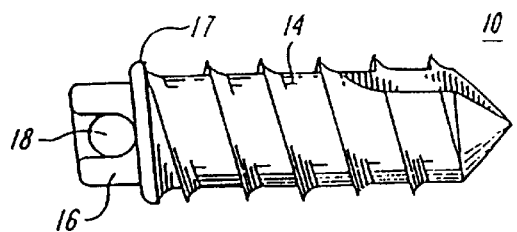
FIG. 10A shows a side plan view of another embodiment of the inventive suture anchor assembly.
Figure 10B:
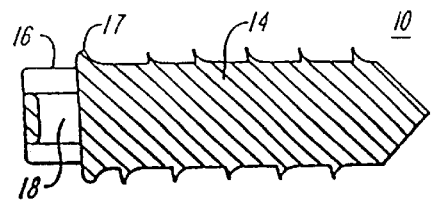
FIG. 10B shows a cross-section of the suture anchor assembly of FIG. 10A.
Figure 9C:
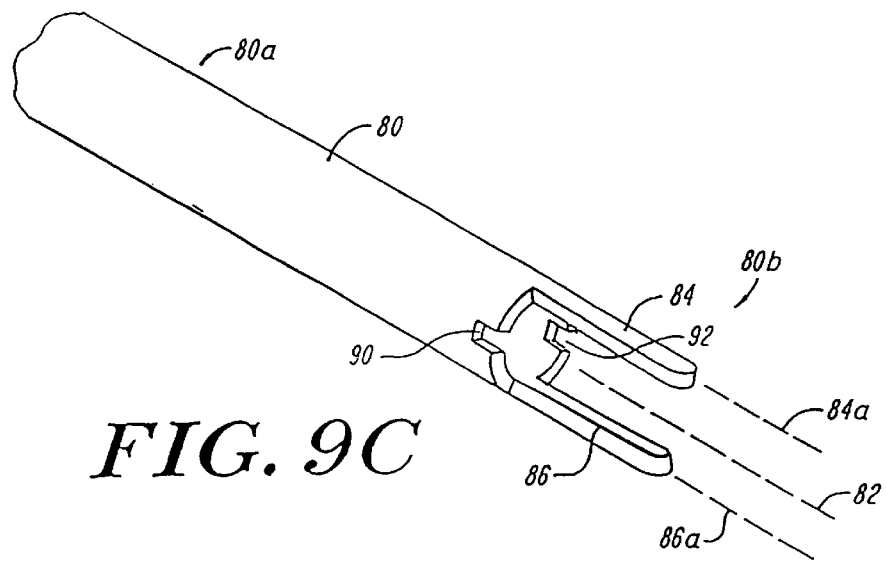
FIG. 9C shows a perspective view of a driver for use with the anchor of FIGS. 9A and 9B.
Figure 9D:
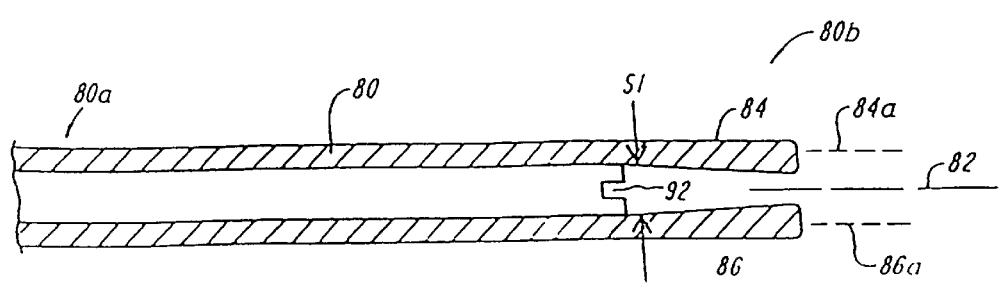
FIG. 9D shows a sectional view of the driver of FIG. 9C.

The embodiment of FIGS. 9A and 9B is particularly adapted for use with the driver 80 shown in FIGS. 9C and 9D. That driver 80 includes an elongated tubular member extending along a driver axis 82 between a proximal end 80a and a distal (or driving) end 80b. A pair of resilient, elongated finger members 84 and 86 extend from the distal end along respective finger axes 84a and 86a, respectively; axes 84a and 86a are substantially coplanar with axis 82. The finger members 84, 86 are shaped so that the anchor 10 of FIGS. 9A and 9B may be supported by the finger members 84, 86, with those finger members fitting within the elongate grooves 26 and 26' in the outside of member 14. The separation S1 of fingers is such that upon placement an anchor 10 between finger members 84, 86 in alignment with grooves 26, 26', the separation S1 between finger members is slightly increased, and the resilient fingers effect a bias force, holding the anchor 10 in place. Thus, the fingers 84, 86 act as spring-biased flexures to support an anchor. Preferably the driver 80 has a pair of slots 90, 92 in its distal top, as shown, which are adapted to receive element 16 upon full insertion of finger members 84, 86 into grooves 26, 26'. With this configuration, a controlled, substantial driving torque may be applied to the drive end of the anchor 10 for insertion.

One aspect of the present invention, and as shown in the figures, is that the anchor portion 14 may include a self-tapping threaded portion. The self-tapping aspect of the threaded anchor portion facilitates insertion of the anchor assembly 10 into a patient's bone or other anchor base at a location desired by the practitioner. Unlike prior art devices that require the creation of an initial insertion hole before introduction of a screw-type anchor, the self-tapping aspect of the threaded portion of the inventive suture anchor assembly allows the user to select the optimal location for insertion of the assembly 10.

Figure 11A:
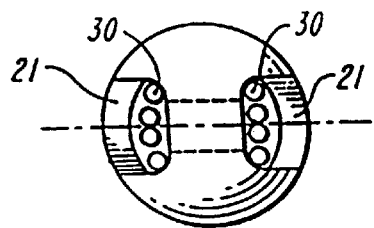
FIG. 11A is an end view of another embodiment of the inventive suture anchor assembly.
Figure 11B:
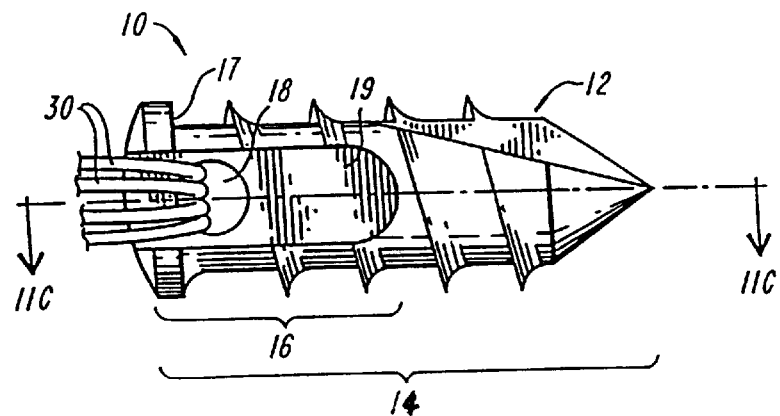
FIG. 11B is a side elevational view of the embodiment of FIG. 11A.
Figure 12A:
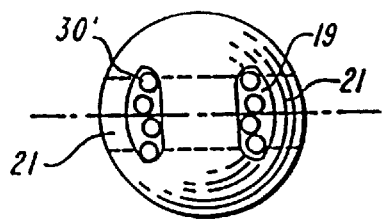
FIG. 12A is an end view of still another embodiment of the inventive suture anchor assembly.
Figure 12B:
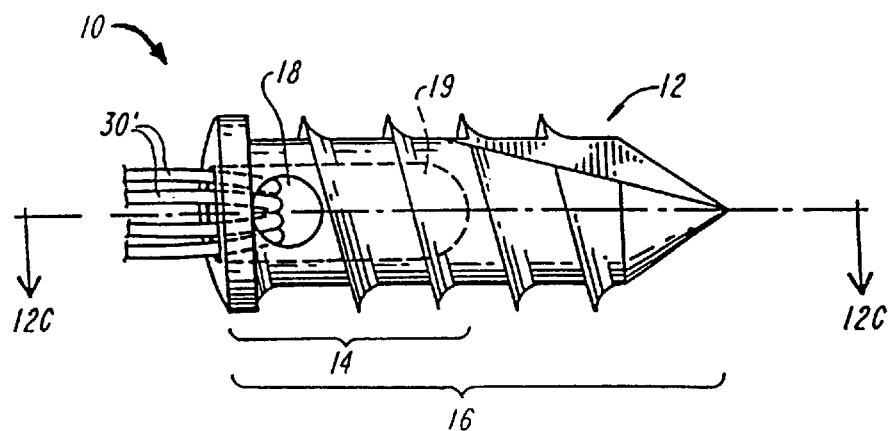
FIG. 12B is a side elevational view of the embodiment of FIG. 12A.

According to another embodiment of the present invention, the anchor portion 14 can have a self-drilling contour at least at points near the first end of the cylindrical member 12, as shown in FIGS. 11B and 12B. The self-drilling contour can include a self-drilling bit at the distal end of the anchor portion 14 for establishing a hole in cancellous and/or cortical bone.

The anchor portion 14 and the suture/drive portion 16 have a continuous self-tapping thread pattern which extends over the outside surface of substantially the entire length of the respective portions, as shown in FIGS. 11B and 12B. The self-tapping thread pattern can extend from the first end to the second end, or from points near the first end to the second end, or from the first end to points near the second end. The self-tapping thread pattern can extend to the outer surface of at least a portion of the self-drilling bit at the distal end of the anchor portion.

The suture anchor 10 can thus be a fully threaded shaft with no head at the suture/drive end 16. Alternatively, the suture anchor can include, for example, a pan head or other flat head formed with shoulder 17, as illustrated in FIGS. 11B, 11C, 12B AND 12C.

Figure 11C:
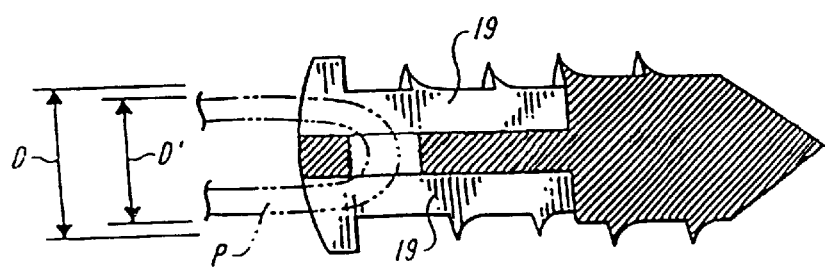
FIG. 11C is a partial longitudinal cross-sectional view of the embodiment of FIG. 11B.
Figure 12C:
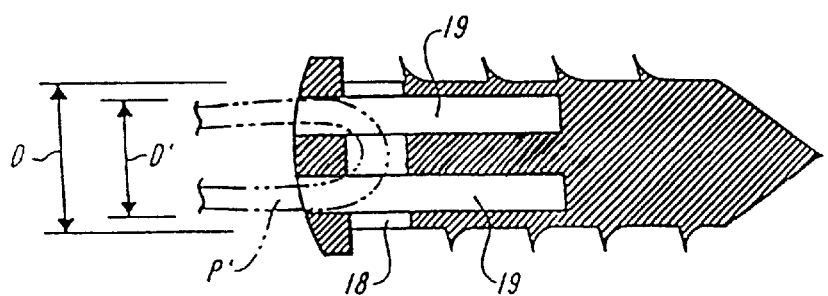
FIG. 12C is a partial longitudinal cross-sectional view of the embodiment of FIG. 12B.

The suture/drive portion 16 includes one or more eyelets 18 positioned at or near the second end. In a preferred embodiment, the eyelet 18 is fully recessed within the elongated cylindrical member, as shown in FIGS. 11B and 11C. As shown in FIGS. 11A–11C, channels 19 are linked by eyelet aperture 18 within the suture/drive portion 16 to define a suture path P. The diameter D' of the suture path P is less than the maximum outer diameter D of the cylindrical member 12, as shown in FIG. 11C. Sutures 30 pass through the channels 19 and eyelet aperture 18 along the suture path P. The channels 19 can be externally located on the outer surfaces of the cylindrical member 12, as shown in FIGS. 11A–C, or they can be internally located within the cylindrical member 12, as shown in FIGS. 12A–12C. The eyelet aperture 18 can be drilled completely through the suture/drive portion 16 at the second end of the suture anchor assembly 10, as shown most clearly in FIG. 12C.

The suture/drive portion 16 includes coupling means for receiving a distal tip 22 of a cannulated driver 20, so that the cylindrical member 12 of the suture anchor assembly and the driver tip 22 can be mechanically coupled for mutual rotation.

Figure 13A:
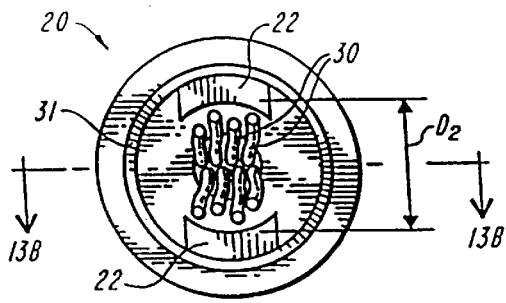
FIG. 13A is an end view of a driver for use with the suture anchor assembly of FIG. 11B.
Figure 13B:
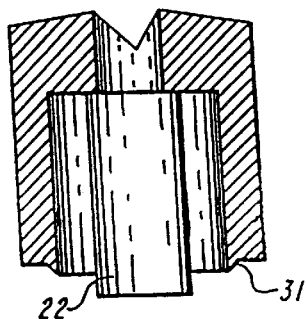
FIG. 13B is a longitudinal cross-sectional view of the driver of FIG. 13A.

FIGS. 13A and 13B show a cannulated driver 20 which can be used with the suture anchor assembly of FIGS. 11A–11C. The suture anchor embodiment of FIGS. 11A–11C features external channels 19 on the outside surfaces of the suture/drive portion 16. The distal tip elements 22 of the cannulated driver 20 have an inner diameter $D_2$ which is greater than or equal to the diameter D' of the suture path P, and an outer diameter $D_3$ which is less than or equal to the maximum outer diameter D of the cylindrical member 12 of the suture anchor. The distal tip elements 22 are adapted to interfit with the channels 19, and to abut surfaces 21 of the suture/drive portion 16, for imparting axial and rotational force to the suture anchor. The distal tip elements 22 of the driver 20 are configured to define a suture path P between them, as shown in FIGS. 11C and 13A.

Figure 14A:
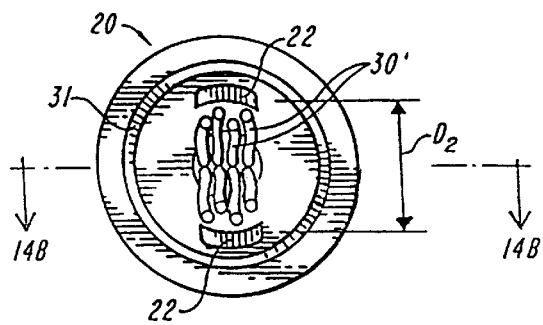
FIG. 14A is an end view of a driver for use with the suture anchor assembly of FIG. 12B.
Figure 14B:
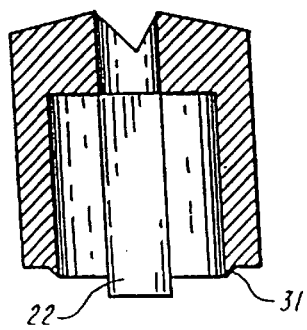
FIG. 14B is a longitudinal cross-sectional view of the driver of FIG. 14A.

FIGS. 14A and 14B show a cannulated driver 20 which can be used with the suture anchor assembly of FIGS. 12A–12C. The suture anchor embodiment of FIGS. 12A–12C features internal channels 19 within the suture/drive portion 16. Note that, relative to the driver 20 of FIG. 13A, the distal tip elements 22 of this driver embodiment are more closely spaced and define a narrower suture path P' between them, as illustrated in FIGS. 12C and 14A. Smaller-gauge sutures 30' must be used with the suture anchor embodiment of FIGS. 12A–12C and the driver embodiment of FIGS. 14A–14B because of the narrower suture path P' and the closer spacing of the channels 19 and the distal tip elements 22 of the driver 20.

The driver 20 further includes an annular tapered leading edge portion 31, as shown in FIGS. 13A–13B and 14A–14B. This tapered leading edge 31 permits the driver 20 to set the suture anchor 10 is slightly (e.g., 1–2 mm) below the top surface of the cancellous bone. When the driver 20 is disengaged from the suture anchor 10 after the anchor is installed in the bone, one or more sutures 30 which remain with the suture anchor 10 contact a gradually tapered edge of bone at the point of entry of the anchor 10 into the bone. This elimination of sharp bone surfaces protects the sutures 20 from premature fraying and also reduces stress on the bone itself.

Figure 15A:
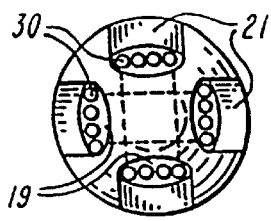
FIG. 15A is an end view of another embodiment of the inventive suture anchor assembly.
Figure 15B:
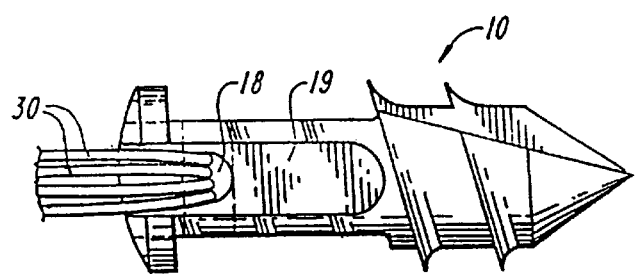
FIG. 15B is a side elevational view of the suture anchor assembly of FIG. 15A.
Figure 15C:
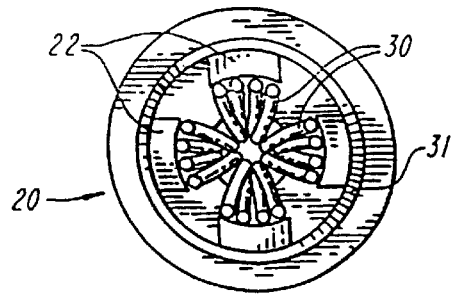
FIG. 15C is an end view of a dirver for use with the suture anchor assembly of FIGS. 15A–15B.
Figure 16A:
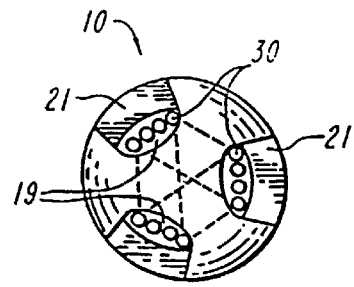
FIG. 16A is an end view of still another embodiment of the inventive suture anchor assembly.
Figure 16B:
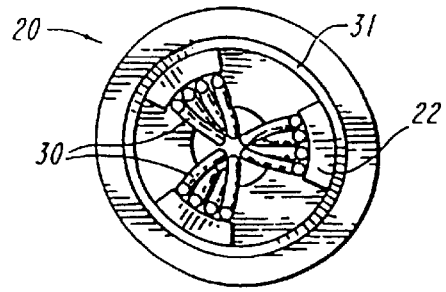
FIG. 16B is an end view of a driver for use with the suture anchor assembly of FIG. 16A.

FIGS. 15A–15B illustrate another suture anchor embodiment in which four external channels 19 are provided in the suture/drive portion. Each of the channels 19 is narrower relative to the channels in the embodiment of FIGS. 11A–11C. A driver 20 for use with this embodiment is illustrated in FIG. 15C. A three-channel embodiment of a suture anchor 10 and corresponding driver 20 is illustrated in FIGS. 16A–16B. Other suture anchor and driver embodiments employing different numbers and arrangements of channels 19 are possible.

The invention may be embodied in other specific forms without departing from the spirit or essential characteristics thereof. The present embodiments and examples are therefore to be considered in all respects as illustrative and not restrictive, the scope of the invention being indicated by the appended claims rather than by the foregoing description, and all changes that come within the meaning and range of equivalency of the claims are therefore intended to be embraced therein.

What is claimed is:

1. A surgical suture anchor assembly, comprising:
    an elongated, generally cylindrical member extending along a central axis and having a maximum outer diameter D, said member including a threaded anchor portion at a first end thereof rigidly coupled to a suture/drive portion at a second end thereof, said second end being opposite said first end,
    wherein said anchor portion has a tip which tapers to a point, and a self-tapping threaded pattern on the outer surface thereof, said pattern extending at least from points near said first end, and:

A. includes at least one eyelet through said suture/drive portion, said eyelet having a central aperture, whereby a suture path extending between two end points is defined by a region adjacent to said second end, through said aperture of said eyelet and back to said region adjacent to said second end, wherein the end points of said suture path are less than a distance equal to D'/2 from said central axis, where D' is less than or equal to said maximum outer diameter D; and
    B. is adapted for insertion into a distal tip of a cannulated driver rotatable about a drive axis,
    whereby said cylindrical member and said distal tip are mechanically coupled for mutual rotation with said drive axis and said central axis being coaxial when said suture/drive portion is inserted into said distal tip of said driver.

2. A suture anchor assembly according to claim 1 further including a cannulated driver wherein said distal tip of said driver has an inner diameter $D_2$ greater than or equal to D'.

3. A suture anchor assembly according to claim 2 wherein said cannulated driver includes an annular tapered leading edge.

4. A suture anchor according to claim 2 wherein said anchor portion includes at least one groove in said cylindrical member near said first end, said groove extending generally parallel to said central axis through at least two turns of said thread pattern.

5. A suture anchor assembly according to claim 1 wherein said distal tip of said driver has an outer diameter $D_3$ less than or equal to D.

6. A suture anchor assembly according to claim 1 further comprising a plurality of sutures extending along said suture path.

7. A suture anchor assembly according to claim 1 wherein said anchor portion has drilling means at a distal tip thereof for establishing a hole in bone.

8. A suture anchor assembly according to claim 7 wherein said thread pattern extends to the outer surface of at least a portion of said drill means at said distal tip of said anchor portion.

9. A suture anchor according to claim 1 further comprising a self-drilling contour at least at points near said first end.

10. A surgical anchor kit, comprising:
    I. an elongated, generally cylindrical member extending along a central axis and having a maximum outer diameter D, said member including a threaded anchor portion at a first end thereof rigidly coupled to a suture/drive portion at a second end thereof, said second end being opposite said first end,
    wherein said anchor portion has a tip which tapers to a point, and a self-tapping thread pattern on the outer surface thereof, said pattern extending at least from points near said first end,
    wherein said suture/drive portion:
    A. includes at least one eyelet through said suture/drive portion, said eyelet having a central aperture, whereby a suture path extending between two end points is defined by a region adjacent to said second end, through said aperture of said eyelet and back to said region adjacent to said second end, wherein the end points of said suture path are less than a distance equal to D'/2 from said central axis, where D' is less than or equal to said maximum outer diameter D; and
    B. is adapted for insertion into a distal tip of a cannulated driver rotatable about a drive axis, whereby said cylindrical member and said distal tip are mechanically coupled for mutual rotation with said drive axis and said central axis being coaxial when said suture/drive portion is inserted into said distal tip of said driver, II. a driver assembly for releasably supporting a suture anchor assembly wherein said driver assembly comprises:
  A. an elongated tubular member extending along a driver axis and having a proximal end and a distal end, and
  B. a pair of resilient, elongated finger members extending from opposite sides of the end of said distal end of said tubular member and along respective finger axes parallel to said driver axis, said finger axes and said driver axes being substantially coplanar, wherein said finger members are separated by a first distance S1 at said distal end of said tubular member and by lesser distances at other locations along said driver axis, and wherein said finger members are adapted to intermit with said channels to define said suture path.

11. A surgical suture anchor assembly, comprising:

an elongated, generally cylindrical member extending along a central axis and having a maximum outer diameter D, said member including a threaded anchor portion at a first end thereof rigidly coupled to a suture/drive portion at a second end thereof, said second end being opposite said first end, wherein said anchor portion has a self tapping thread pattern on the outer surface of said anchor portion, said pattern extending from said first end, and wherein said anchor portion has a cylindrical barrel bearing said thread pattern, wherein said suture/drive portion:
  A. includes at least one eyelet positioned at or near said second end, said eyelet having a central aperture, whereby a suture path extending between two end points is defined by a region adjacent to said second end, through said aperture of said eyelet and back to said region adjacent to said second end, wherein the end points of said suture path are less than a distance equal to $D'/2$ from said central axis, where $D'$ is less than or equal to said maximum outer diameter D; and
  B. is adapted fro insertion into a distal tip of a cannulated driver rotatable about a drive axis, whereby said cylindrical member and said distal tip are mechanically coupled for mutual rotation with said drive axis and said central axis being coaxial when said distal tip of said driver is inserted into said distal tip of said driver.

12. A suture anchor according to claim 11, wherein said anchor portion includes at least one fluted region near said first end and overlapping said thread pattern.

13. A suture anchor assembly according to claim 12 further including a annulated driver wherein said distal tip of said driver has an inner diameter greater than or equal to $D'$.

* * * * *